(12) United States Patent
Mam et al.

(10) Patent No.: US 6,602,207 B1
(45) Date of Patent: Aug. 5, 2003

(54) GUIDE WIRE STIFFNESS TRANSITION ELEMENT

(75) Inventors: Sovann V. Mam, Lynn, MA (US); Maura Rooney, Arlington, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 200 days.

(21) Appl. No.: 09/620,263

(22) Filed: Jul. 19, 2000

(51) Int. Cl.[7] ................................................ A61B 5/00
(52) U.S. Cl. ...................................... 600/585; 604/525
(58) Field of Search ............................... 600/433, 434, 600/585; 604/523–525, 528

(56) References Cited

U.S. PATENT DOCUMENTS

| | | | |
|---|---|---|---|
| 4,534,363 A | 8/1985 | Gold ........................... | 128/772 |
| 4,721,117 A | 1/1988 | Mar et al. .................... | 128/772 |
| 4,748,986 A | 6/1988 | Morrison et al. ........... | 128/772 |
| 4,841,976 A | 6/1989 | Packard et al. | |
| 4,984,581 A | 1/1991 | Stice ........................... | 128/772 |
| 5,065,769 A | 11/1991 | de Toledo | |
| 5,147,317 A | 9/1992 | Shank et al. | |
| 5,213,111 A | 5/1993 | Cook et al. | |
| 5,228,453 A | 7/1993 | Sepetka ....................... | 128/772 |
| 5,365,942 A | 11/1994 | Shank ......................... | 128/772 |
| 5,372,144 A | 12/1994 | Mortier et al. | |
| 5,498,250 A | 3/1996 | Prather ....................... | 604/280 |
| 5,664,580 A | 9/1997 | Erickson et al. ............. | 128/772 |
| 5,769,796 A | 6/1998 | Palermo et al. ............. | 600/585 |
| 5,788,654 A | 8/1998 | Schwager | |
| 5,797,856 A | 8/1998 | Frisbie et al. | |
| 5,885,227 A | 3/1999 | Finlayson | |
| 5,924,998 A | 7/1999 | Cornelius et al. ........... | 600/585 |
| 5,957,903 A * | 9/1999 | Mirzaee et al. ............. | 604/524 |
| 6,004,279 A | 12/1999 | Crowley et al. | |
| 6,027,460 A | 2/2000 | Shturman .................... | 600/585 |
| 6,039,699 A | 3/2000 | Viera | |
| 6,132,388 A * | 10/2000 | Fleming et al. ............. | 600/585 |
| 6,308,090 B1 * | 10/2001 | Tu et al. ...................... | 600/585 |
| 6,402,706 B2 * | 6/2002 | Richardson et al. ........ | 600/585 |

FOREIGN PATENT DOCUMENTS

WO 99/58183 11/1999

OTHER PUBLICATIONS

"Clinical Basis for Guidewire Selection", Boston Scientific Corporation.

* cited by examiner

Primary Examiner—J. Casimer Jacyna
(74) Attorney, Agent, or Firm—Testa, Hurwitz & Thibeault LLP

(57) ABSTRACT

Disclosed is a guide wire having a coil surrounding a core of the guide wire and a stiffness transition element. The stiffness transition element is configured to provide a smooth stiffness transition from the distal end of the guide wire to the coil and/or the core of the guide wire. The stiffness transition element may be formed of any medical grade polymer.

19 Claims, 3 Drawing Sheets

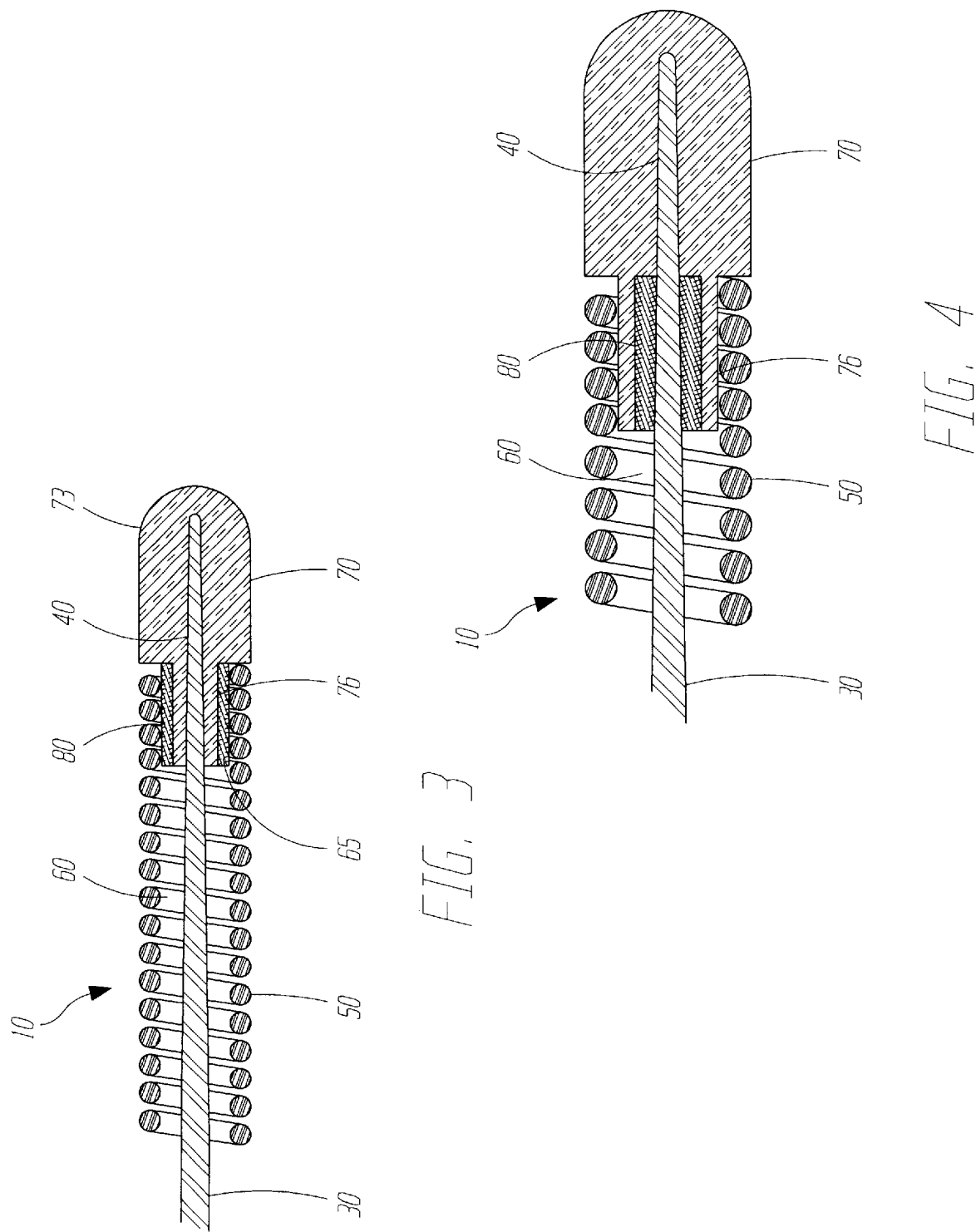

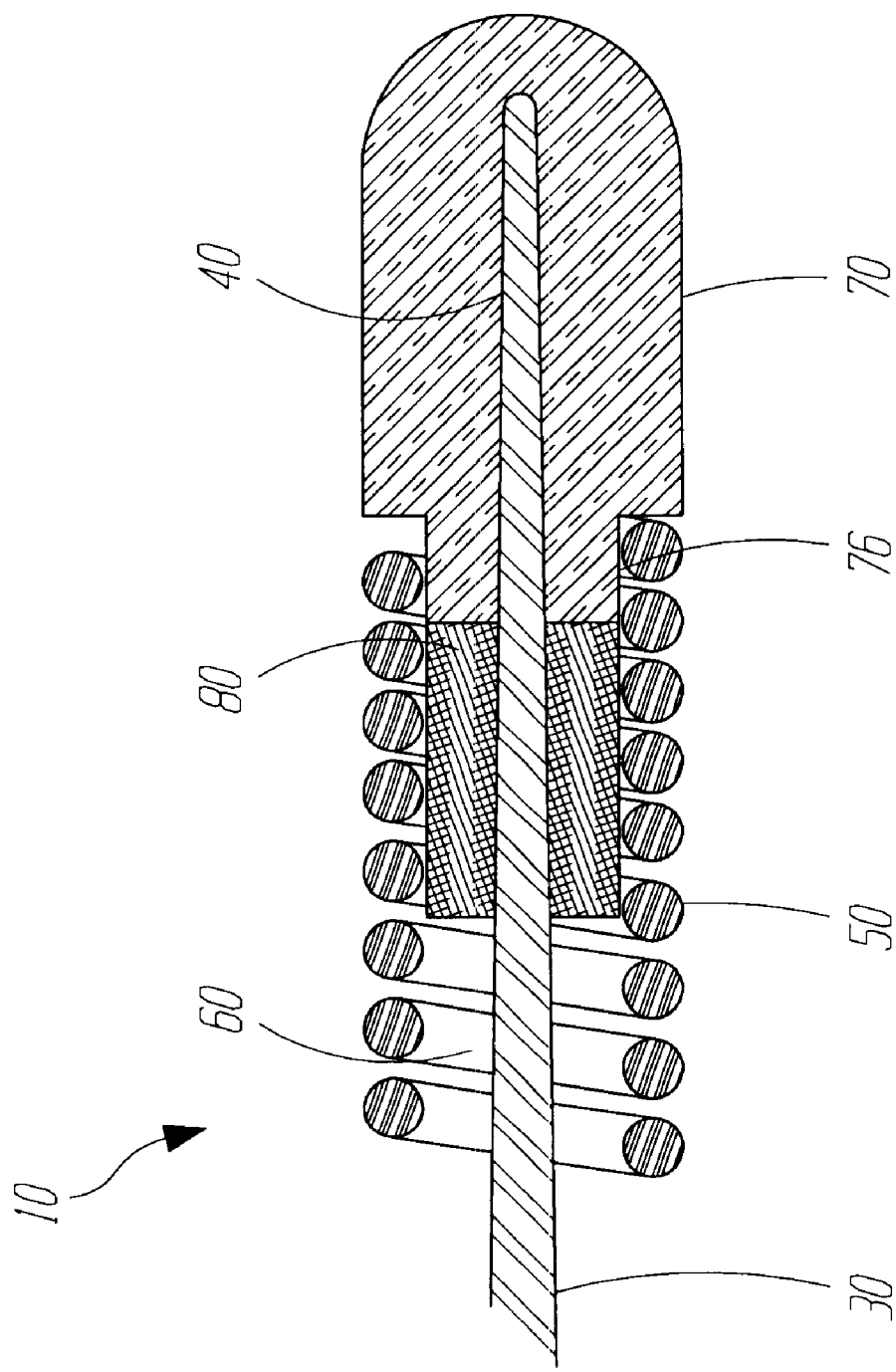

GUIDE WIRE STIFFNESS TRANSITION ELEMENT

FIELD OF THE INVENTION

The present invention generally relates to guide wires. More specifically, the invention relates to a novel approach to making a smoother transition in stiffness along the length of a guide wire which is more stiff at the proximal end and less stiff at the distal end. Those skilled in the art will recognize the benefits of applying the present invention to similar fields not discussed herein.

BACKGROUND OF THE INVENTION

Guide wires are used in a variety of medical applications including intravascular, gastrointestinal, and urological. A common vascular application is Percutaneous Transluminal Coronary Angioplasty (PTCA). This procedure can involve inserting a guide wire through an incision in the femoral artery near the groin, advancing the guide wire over the aortic arch, into a coronary artery, and across a lesion to be treated in the heart. Similarly, angioplasty performed in other parts of the anatomy is called Percutaneous Transluminal Angioplasty (PTA) and may also involve the use of a guide wire. Typical vascular guide wires are 50 cm or 300 cm in length, and are 0.010–0.038 inches in diameter depending upon the application.

Common gastrointestinal uses of guide wires include endoscopic procedures in which an endoscope may be inserted into the mouth and advanced through the esophagus to the bile duct, the cystic duct, or the pancreatic duct. A guide wire is then threaded through a lumen in the endoscope and into the bile duct, cystic duct, or pancreatic duct. Once the distal tip of the guide wire is located in a position desired to be treated, a catheter having a medical instrument on it distal end is advanced over the guide wire and to the treatment area. The guide wire and the catheter may then be observed through the endoscope as treatment occurs.

Urological uses of guide wires include the placement of ureteral stents. Ureteral stenting is required when the normal flow of urine from the kidney into the bladder is compromised perhaps by tumor growth, stricture, or stones. Generally, the procedure involves the insertion of a ureteroscope through the urethra and into the bladder. A guide wire is then advanced through the ureteroscope and into a ureter. The wire is then forced through the compromised portion of the ureter. Once the guide wire is in place, a ureteral stent is advanced over the guide wire and into position in the ureter. The guide wire may then be removed and the stent will maintain the patency of the fluid path between the kidney and the bladder. The procedures described above are but a few of the known uses for guide wires.

Pushability, kink resistance, torqueability and bendability are closely related and important features of a guide wire. It is important that force applied at the proximal end of a guide wire is completely transferred to the distal end of the guide wire. A guide wire must exhibit good bendability. This characteristic is a balance between adequate flexibility to navigate a tortuous lumen and suitable rigidity to support tracking of another device such as a catheter. Torqueability is closely related to the torsional rigidity of the wire and is ultimately demonstrated by how well rotation imparted to the proximal end of the guide wire is translated to the distal end of the guide wire.

Kink resistance is also an important characteristic of a guide wire. Kink resistance is closely related to the stiffness of the wire. Very stiff wires often provide good pushability (axial rigidity) but poor kink resistance. Kink resistance is measured by the ability of the guide wire to be forced into a relatively tight bend radius without permanently deforming the wire.

Many guide wires use stiffness by creating a transition from relatively more stiff in the proximal end to relatively less stiff in the distal end. This provides the best combination of pushability and the ability to navigate tortuous vessels. The transition in stiffness may easily be seen by simply bending the wire about an arch. FIG. 1 depicts a prior art wire 10 which shows with a flat spot 20 in the arch of the wire. A potential kink point may be created where the transition is not smooth. Furthermore, the unsmooth or flat transition region causes resistance when the wire is advanced through a vessel. The ideal transition is a smooth and continuous transition from stiffer to less stiff. The ideal transition is depicted in FIG. 2 where wire forms a smooth and continuous arch.

Several different types of guide wires are well known in the art. One type of wire is characterized by a solid metal core surrounded by a metal coil. Typical metals for the core may include spring steels and stainless steels. The distal tip of the core may also be ground to a taper to provide added flexibility near the tip. Coils may be made of the same variety of metals used as core materials. The coil may be made of round wire or flat wire and may surround the entire length of the core or only a portion of the core. The coil usually is formed by helically wrapping the wire around a mandrel, removing the mandrel, and inserting the core into the coil. The pitch of the wire may be varied along the length of the coil to vary the stiffness of the coil.

Traditional coil over core wires provide good axial stiffness and hence improved possibility. Traditional coil over core wires also provide dramatically improved kink resistance over stainless steel wires and achieve a smooth transition in stiffness by using a ground core. Some coil over core wires also use a polymer jacket or sleeve to provide improved lubricity and wire movement. However, a flat spot in the stiffness transition may be created where the sleeve stops leaving only the coil over core construction. A coil over core wire having at least a portion covered by a polymer would therefore be improved if it had a smoother transition near the termination of the polymer sleeve.

SUMMARY OF THE INVENTION

The present invention improves upon the prior art by providing a coil over core guide wire having a smooth stiffness transition.

BRIEF DESCRIPTION OF THE DRAWINGS

FIG. 3 depicts an embodiment of the invention.

FIG. 4 depicts another embodiment of the invention.

FIG. 5 depicts another embodiment of the invention.

DETAILED DESCRIPTION OF THE INVENTION

Figure 1:
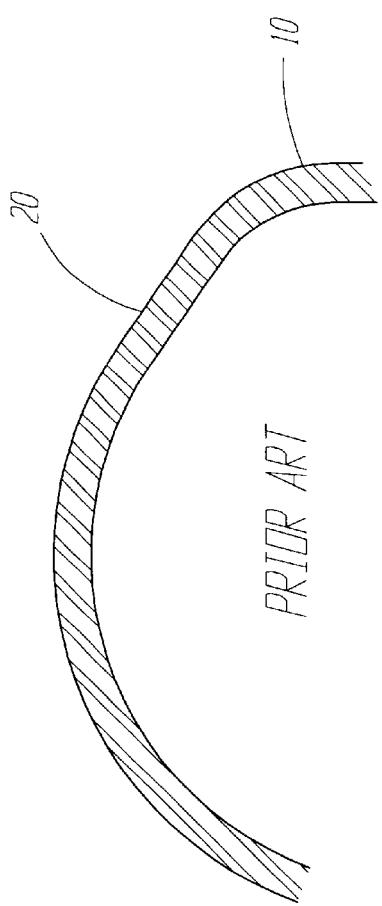
FIG. 1 depicts a prior art guide wire bent about an arch.
Figure 2:
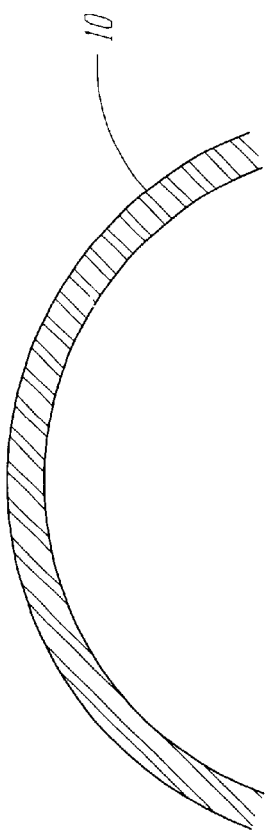
FIG. 2 depicts an ideal guide wire bent about an arch.

The following detailed description should be read with reference to the drawings in which like elements in different drawing are numbered identically. The drawings, which are not necessarily to scale, depict selected embodiments and are not intended to limit the scope of the invention.

Examples of constructions, materials, dimensions, and manufacturing processes are provided for selected elements.

All other elements employ that which is known to those skilled in the field of the invention. Those skilled in the art will recognize that many of the examples provided have suitable alternatives that may also be used.

Construction of a coil over core guide wire is described in copending patent application Ser. No. 09/078,946, filed May 14, 1998, which is herein incorporated by reference.

FIG. 3 depicts an embodiment of the invention where core wire may be formed of any biocompatible plastic or metal. Core wire 30 may be formed of a variety of metals including stainless steals such as 316, Eligiloy, or MP35N. Core wire 30 may also be formed of alloys of nickel and titanium such as Nitinol where the nickel titanium alloy is heat treated such that the wire is linearly elastic or superelastic. Core wire 30 may be about 125–300 cm in length and may further have a tapered distal portion 40.

Surrounding core wire 30 may be a coil 50. Coil 50 may be formed of any biocompatible metal or plastic. Coil 50 may be formed of stainless steals or nickel titanium alloys. Coil 50 may be formed of flat ribbon or wire that is ovoid, rectangular or round in cross-section. Coil 50 may have tightly packed turns where each turn touches the preceding turn or may have loosely spaced turns. Coil 50 may further have turns which change in spacing or which change in pitch along the length of coil 50.

Coil 50 may have an interior diameter which is greater than the outside diameter of core wire 30 or may have an interior diameter which is approximately equal to the outside diameter of core wire 30. The diameter of coil 50 may vary along the length of the coil. In a preferred embodiment, the coil 50 may have a uniform diameter along its entire length. Where core wire 30 has a tapered portion 40, the inside diameter of the coil 50 may be greater than the outside diameter of the tapered portion 40 which thereby forms an annular space 60.

Surrounding tapered portion 40 is polymer tip 70. Polymer tip 70 may best, formed of any suitable medical grade polymer including Plexar, nylon, polypropylene, polyurethane, polyethylene, silicone and polyether glycol. In a preferred embodiment, polymer tip 70 may be formed from urethane. Tip 70 has a distal portion 73 and a proximal portion 76 where distal portion 73 may generally be of a diameter approximately equal to the outside diameter of coil 50 and proximal portion 76 may generally have a outside diameter less than the inside diameter of coil 50. Second annular space 65 may be formed between the outside of proximal portion 76 and the inside of coil 50.

Annular space 65 may be filled with a transition element 80. Transition element 80 may be formed of any suitable medical grade polymer including silicone. In a preferred embodiment, transition element 80 may be formed of a polymer having a hardness that is less than the hardness of tip 76 where tip 76 may be about 45 D and transition element 80 may be approximately 25 D.

Wire 10 may be assembled by placing transition element 80 about proximal portion 76 and then sliding the assembled tip 70 and transition element 80 over core 30 and into annular space 60. Following this step, the entire assembly may be bond together using common bonding practices including adhesives. Alternatively, wire 10 may be heated to cause transition element 80 and polymer tip 70 to flow together. Transition element 80 and polymer tip 70 may also flow into coil 50 and ultimately become bonded to wire 10.

Alternatively, polymer tip 70 may be formed without proximal portion 76 (not shown). Wire 10 may then be assembled by placing transition element 80 into annular space 60. Tip 70 may then be place about core 30. Wire 10 may then be subject to heating sufficient to cause polymer tip 70 to flow into the annular space formed between the inside diameter of transition element 80 and core 30. Ultimately then, transition element 80 may bond to core 30, coil 50 and tip 70.

FIG. 4 depicts an alternative embodiment of the invention where like elements are similarly numbered. In this embodiment, transition element 80 may be formed to closely fit about tapered portion 40. The outside diameter of transition element 80 may be sized such that an annular space is formed between transition element 80 and the inside diameter of coil 50. Polymer tip 70 may then have a proximal section 76 which may fit into the annular space formed between the outside diameter of transition element 80 and the inside diameter of coil 50. The entire assembly may then be bonded as previously described. Alternatively, polymer tip 70 may be formed without proximal section 76 (not shown) and heated such that polymer tip 70 flows into the annular space formed between the outside diameter of transition element 80 and the inside diameter of coil 50.

FIG. 5 depicts another embodiment of the invention where like elements are similarly numbered. In this embodiment, transition element 80 may be closely formed to fit about tapered portion 40. Transition element 80 may further have an outside diameter which may approximately the same as the inside diameter of coil 60. Transition element 80 may be positioned about tapered portion 40 such that the distal end of transition element does not match with the distal end of coil 60 and thereby leaves an annular space distal of transition element 80 which is formed by the space between the outside diameter of tapered section 40 and the inside diameter of coil 60. Polymer tip 70 may then be formed with a proximal portion 76 sized to fit in the annular space formed by the space between the outside diameter of tapered section 40 and the inside diameter of coil 60. The entire tip assembly may then be bonded as previously described.

Polymer tip 70 may be formed without a proximal section 76 (not shown). The tip assembly may then be bonded by heating wire 10 such that polymer tip 70 flows into the annular space formed by the space between the outside diameter of tapered section 40 and the inside diameter of coil 60.

Alternatively, transition element 80 may have its distal end aligned with the distal end of coil 50. The tip assembly may then be bonded as described above.

While the specification describes the preferred designs, materials, methods of manufacture and methods of use, those skilled in the art will appreciate the scope and spirit of the invention with reference to the appended claims.

We claim:

1. A guide wire comprising:
   an elongate body having a distal end;
   a coil comprising successive turns, the coil surrounding at least a distal portion of the elongate body; and
   a transition element configured to provide a smooth stiffness transition from the distal end of the elongate body to the coil.

2. The guide wire of claim 1 where in the elongate body comprises:
   a first stiffness near the distal end; and
   a second stiffness proximal to the distal end, the second stiffness being greater than the first stiffness.

3. The guide wire of claim 1 wherein the coil surrounds all of the elongate body proximal of the distal end of the elongate body.

4. The guide wire of claim 1 further comprising:
a polymer tip, the tip surrounding the distal end of the elongate body.

5. The guide wire of claim 4 wherein:
the coil has an inside diameter larger than a diameter of the elongate body with an annular space therebetween; and
the transition element at least partially fills the annular space.

6. The guide wire of claim 5 wherein a portion of the polymer tip fills a portion of the annular space between the coil and the elongate body.

7. The guide wire of claim 6 wherein the polymer tip surrounds the transition element.

8. The guide wire of claim 6 wherein the transition element surrounds the polymer tip.

9. The guide wire of claim 6 wherein the polymer tip abuts the transition element.

10. A guide wire comprising:
a polymer distal tip, configured to provide an atraumatic distal end to the guide wire;
a wire member, embedded in the polymer tip and extending proximal of the polymer tip;
a coil surrounding at least a portion of the polymer tip; and
a transition element positioned about the wire member such that the transition element provides a smooth stiffness transition from the polymer tip to the coil.

11. The wire member of claim 10 having a proximal section and a distal section, the proximal section stiffer than the distal section.

12. The guide wire of claim 10 wherein the transition element surrounds a portion of the polymer tip.

13. The guide wire of claim 10 wherein the polymer tip surrounds a portion of the transition element.

14. The guide wire of claim 10 wherein the transition element abuts the polymer tip.

15. A guide wire comprising:
an elongate body, the elongate body having a stiffness;
a tip affixed to a distal end of the elongated body, the tip having a stiffness;
means for transitioning the stiffness of the tip to the stiffness of the elongate body;
and a coil surrounding at least a portion of the elongate body.

16. The guide wire of claim 15 wherein the coil surround a portion of the transition means.

17. The guide wire of claim 15 wherein the coil surrounds a portion of the tip.

18. The guide wire of claim 15 wherein the coil surrounds a portion of the tip and a portion of the transition means.

19. A guide wire comprising:
an elongate body, the elongate body having a stiffness;
a tip affixed to a distal end of the elongated body, the tip having a stiffness;
means for transitioning the stiffness of the tip to the stiffness of the elongate body,
wherein the tip surrounds a portion of the transition means.

* * * * *